United States Patent [19]
Fowler, Jr.

[11] Patent Number: 5,899,853
[45] Date of Patent: May 4, 1999

[54] DOUBLE GRIP SURGICAL RETRACTOR STAY

[75] Inventor: James M. Fowler, Jr., Houston, Tex.

[73] Assignee: Lone Star Medical Products, Inc., Houston, Tex.

[21] Appl. No.: 09/075,779

[22] Filed: May 11, 1998

[51] Int. Cl.[6] .................................................. A61B 17/02
[52] U.S. Cl. ............................................ 600/217; 600/218
[58] Field of Search ................................ 600/206, 217, 600/209, 233, 218

[56] References Cited

U.S. PATENT DOCUMENTS

| | | | |
|---|---|---|---|
| Re. 32,021 | 11/1985 | Scott, Jr. | 600/233 |
| 3,762,401 | 10/1973 | Tupper | 600/217 |
| 4,430,991 | 2/1984 | Darnell . | |
| 5,337,736 | 8/1994 | Reddy | 600/217 |
| 5,788,649 | 7/1998 | Fowler, Jr. | 600/217 |

*Primary Examiner*—Paul J. Hirsch
*Attorney, Agent, or Firm*—Akin, Gump, Strauss, Hauer & Feld, L.L.P.

[57] ABSTRACT

A surgical retractor includes an elongated elastic member having first and second end portions. A retractor hook portion is connected to the first end portion of the elastic member. The second end of the elastic member has a receptacle for connecting a pair of jaws thereto. A pair of jaws is provided, each being mounted to the elastic member at the receptacle. A jaw closing member is provided for urging the jaws to clamp together in a "closed" position. Two sockets are provided in the receptacle, each of the sockets accepting one of the jaws. A portion of the elastic member is positioned in between the two jaws to provide elasticity that urges the jaws to clamp the jaw together.

30 Claims, 3 Drawing Sheets

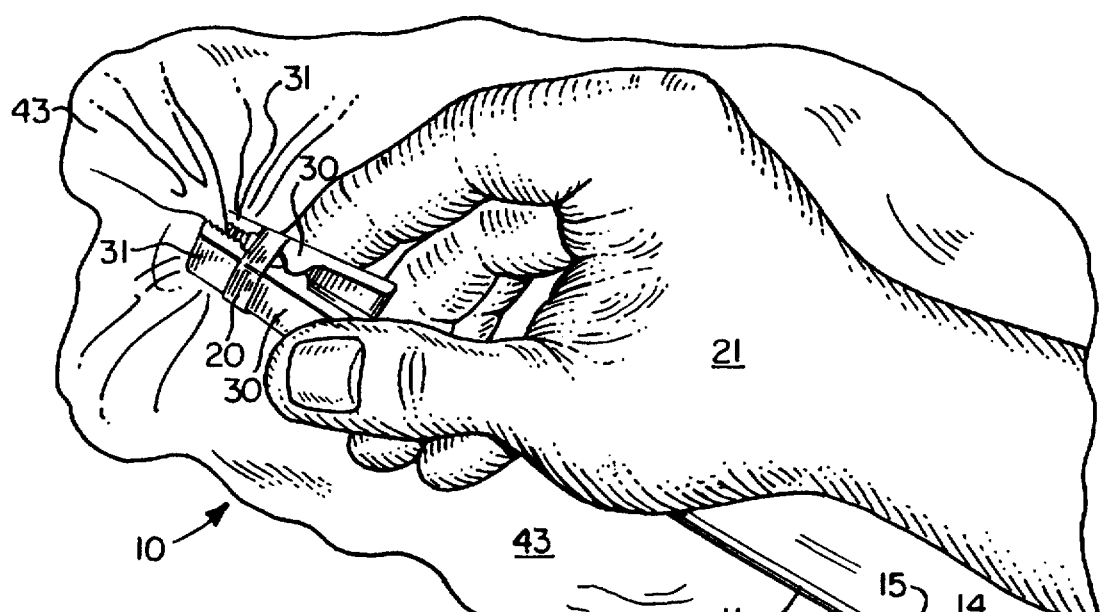
FIG. 1.
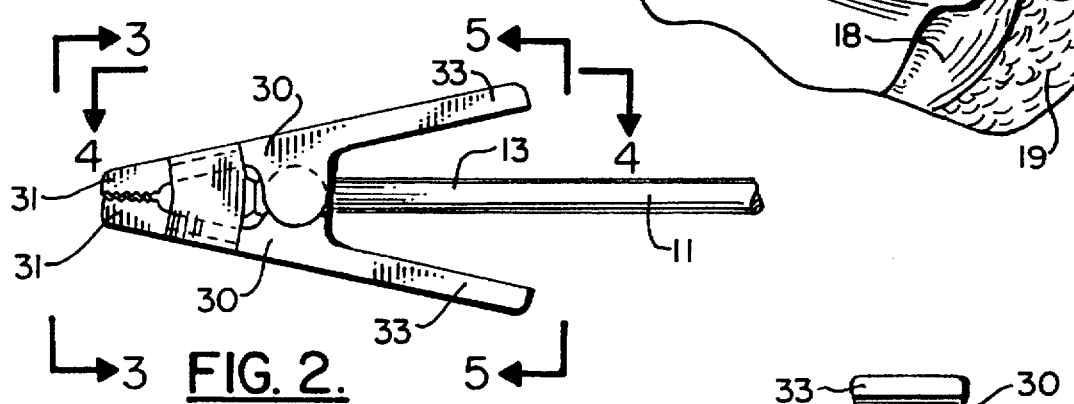
FIG. 2.
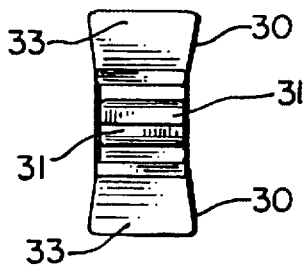
FIG. 3.
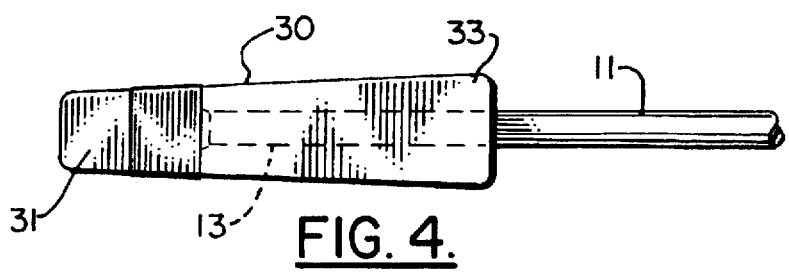
FIG. 4.
FIG. 5.

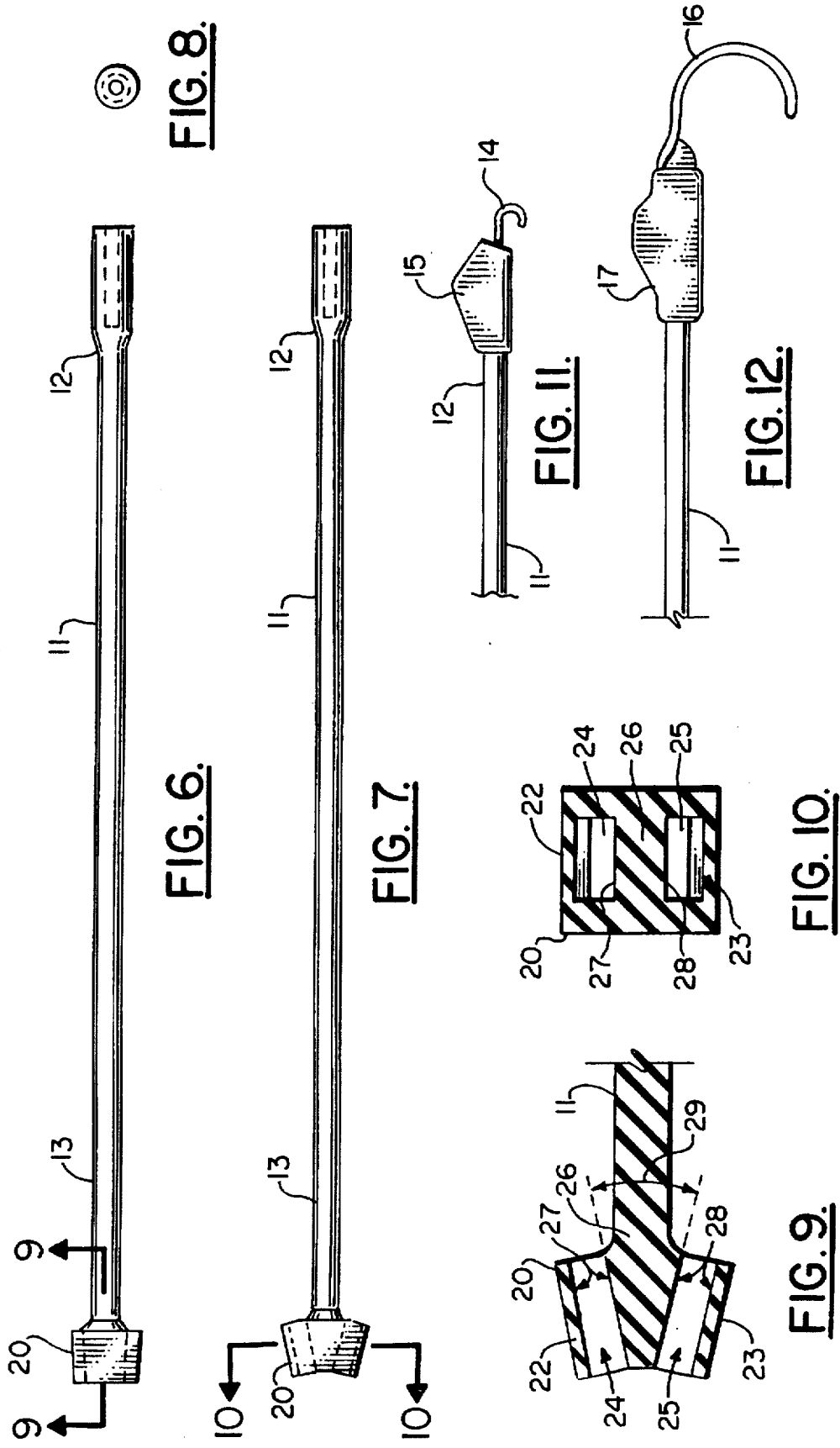

5,899,853

DOUBLE GRIP SURGICAL RETRACTOR STAY

CROSS-REFERENCE TO RELATED APPLICATIONS

Not applicable.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to surgical retractors, and more particularly to an improved double grip surgical retractor stay that can be used in surgery for retracting tissue at an incision, wherein one end portion of the stay includes a hook portion for engaging the tissue to be retracted, the opposing end portion having a receptacle that carries jaws that enable attachment of the retractor to surgical drape material.

2. General Background of the Invention

Many types of surgeries have surgical sites that require numerous retractors to hold the incision open. In some situations, the retractor must necessarily include a very small stay for holding the incision open in a restricted area. Such a retractor stay construction is shown in U.S. Pat. No. 4,430,991, issued to Darnell and entitled "Surgical Retractor Stay Device And Tube Connector". The Darnell patent provides a frame that accepts one end portion of an elastic tubular member. The other end of the tubular member carries a hook construction for engaging the selected tissue.

In some surgical procedures, the particular geometry presented does not allow for the use of a retractor ring of the type shown in the Darnell '991 patent at the wound site. However, the elastic stay that is shown in the Darnell patent continues to provide benefit to the surgeon even when the retractor ring cannot be fitted to the wound site. Currently, surgeons are using the elastic stays shown in the Darnell '991 patent by clamping the tail end of the elastic stay to a surgical drape using a hemostat or forceps. In order to clamp the elastic stay tail of the Darnell '991 patent type of stay using a hemostat or forceps, such could require up to three hands. One hand is needed to hold the hemostat and forceps. One hand is needed to pull the elastic stay tail. Yet a third hand must position the drape.

A further disadvantage of the current method arises from the hemostat or forceps handles being placed around the wound site. In some case, there may be as many as 10 or 12 hemostats or forceps in use, substantially cluttering the operating area or surgical site.

BRIEF SUMMARY OF THE INVENTION

The present invention provides an improved surgical retractor construction that includes an elongated elastic member that has first and second end portions. One of the end portions carries a retractor hook portion for retracting tissue at a surgical site. The other end of the elastic member has a receptacle for connecting jaws thereto. These jaws can be used to grip surgical drape material for anchoring the stay without cluttering the operating area with hemostats and/or forceps.

In the preferred embodiment, a pair of jaws is provided, each mounted to the elastic member at the receptacle at the second end of the elastic member.

In the preferred embodiment, there are two sockets at one end of the elastic member and a pair of jaws are attached to the elastic member at the pair of sockets.

The elastic member provides elasticity that actually urges the jaws to clamp together.

Each jaw pivots upon the other, eliminating a third "pivot" member. Rather, the jaws themselves carry the pivoting connection that is perfected when the jaws are affixed to the sockets.

The jaws pivot one upon the other at cooperating concave and convex articulating surfaces.

Each of the jaws provides a gripping tip portion so that when the jaws are closed, the jaw tips engage one another. The jaw closing member is positioned in between the jaw tips and the articulating surfaces. The jaw closing member is preferably in the form of a portion of the elastic member that encircles the jaws to provide elasticity that holds the jaws together. The jaws can be forced apart when the surgeon wants to grip drape material, each jaw having a handle.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 1 is a perspective view of the preferred embodiment of the apparatus of the present invention;

FIG. 2 is an partial elevational view of the preferred embodiment of the apparatus of the present invention;

FIG. 3 is a partial end view of the preferred embodiment of the apparatus of the present invention, taken along lines 3—3 of FIG. 2;

FIG. 4 is a partial top view of the preferred embodiment of the apparatus of the present invention taken along lines 4—4 of FIG. 2;

FIG. 5 is a sectional view taken along lines 5—5 of FIG. 2;

FIG. 6 is a partial top view of the preferred embodiment of the apparatus of the present invention illustrating the elastic member portion thereof;

FIG. 7 is a partial elevational view of the preferred embodiment of the apparatus of the present invention illustrating the elastic member portion thereof;

FIG. 8 is an end view of the elastic member of FIG. 7;

FIG. 9 is a sectional view taken along lines 9—9 of FIG. 7;

FIG. 10 is a sectional view taken along lines 10—10 of FIG. 7;

FIG. 11 is a partial elevational view of the preferred embodiment of the apparatus of the present invention showing a smaller hook portion for retracting tissue;

FIG. 12 is another fragmentary elevational view of the preferred embodiment of the apparatus of the present invention showing a larger hook portion for retracting tissue;

DETAILED DESCRIPTION OF THE INVENTION

Figure 14:
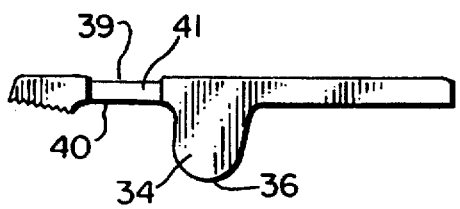
FIG. 14 is a side elevational view of a jaw portion of the preferred embodiment of the apparatus of the present invention.

FIG. 1 shows generally the preferred embodiment of the apparatus of the present invention designated generally by the numeral 10 in FIG. 1. Surgical stay apparatus 10 includes an elongated elastic member 11 (see FIGS. 6–12) that can be a tubular member having a first end 12 and a second end 13. Hook 14 (see FIGS. 1, 11, 12) is held by first end 12. Handle 15 forms a connection that holds hook 14 to elastic member 11. A second type of hook 16 (see FIG. 12) can, for example, be a wider hook member having multiple hooks such as two or four hook portions. Handle 17 engages hook 16 to hold it to the end of elastic member 11.

The hooks 14, 16 or another type of similar hook construction can be used to engage the patient's tissue 18 at a surgical site or surgical opening or wound 19.

Figure 17:
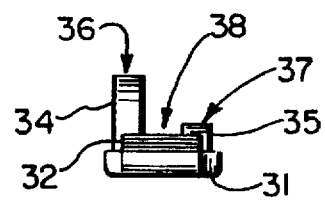
FIG. 17 is an end view of the jaw portion of the preferred embodiment of the apparatus of the present invention taken along lines 17—17 of FIG. 16.
Figure 15:
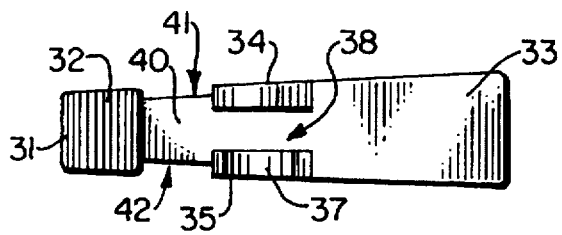
FIG. 15 is a fragmentary view of the jaw portion of the preferred embodiment of the apparatus of the present invention.
Figure 16:
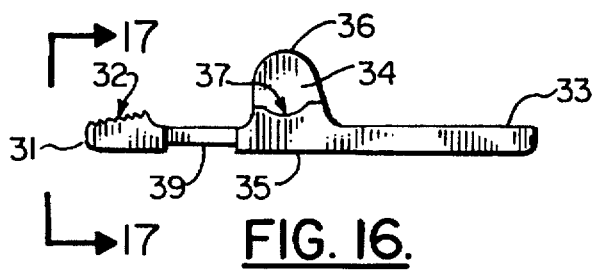
FIG. 16 is an elevational view of the jaw portion of the preferred embodiment of the apparatus of the present invention.
Figure 13:
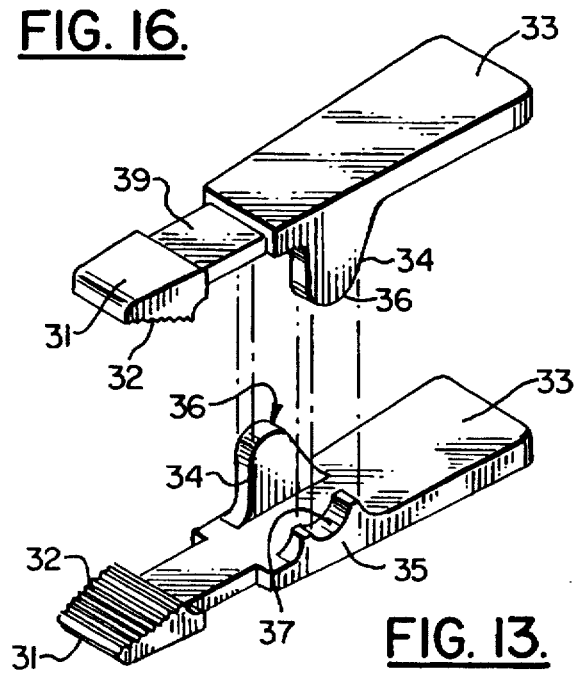
FIG. 13 is a partial perspective, exploded view of the preferred embodiment of the apparatus of the present invention illustrating the jaw portions thereof.

An end portion 13 of elastic member 11 opposite the end 12 that carries a hook 14 or 16 can be seen in FIGS. 1, 2–5 and 13–17 as having a receptacle 20 carrying jaws 30. The receptacle 20 includes inclined outer walls 22 and 23 and rectangular sockets 24 and 25. The receptacle 20 also includes an elastic central section 26 that provides elasticity for holding a pair of jaws 30 together as shown in FIGS. 1 and 2. Jaws 30 can grip drape material 43 that surrounds the wound opening 19 when the jaws 30 are manipulated by a user's hand 21 (see FIG. 1). An angle 29 is formed between the side walls 27 and 28 that defines the angle also between the jaws 30 when they are inserted into rectangular sockets 24 and 25.

In FIG. 1–5 and 13–17, each jaw 30 provides a jaw tip 31 having serrated gripping surfaces 32 thereon. Each jaw 30 provides a widened flange 33 opposite jaw tip 31 that can be gripped by a user's hand 21 in order to open the jaws when it is desired to grip surgical drape material with the jaws 30. The two jaws 30 are hingedly connected together once they are assembled to the rectangular sockets 24, 25 of receptacle 20. A pair of hinged members 34, 35 form the pivotal engagement between the two jaws 30 when in operating positions in receptacle 20.

One of the hinged members includes a convex articulating surface 36. The other hinged member 35 includes a concave articulating surface 37. Channel 38 forms an open space in between the hinged members 34 and 35 through which elongated elastic member 11 passes when the apparatus 10 is assembled (see FIGS. 2, 5 and 13–17). Each jaw 30 provides four receptacle engaging surfaces 39, 40, 41, 42 that engage the walls 22, 23 and side walls 27, 28 of receptacle 20 upon assembly (see FIGS. 2–10 and 13–17).

The following table lists the parts numbers and parts descriptions as used herein and in the drawings attached hereto.

PARTS LIST

| Part Number | Description |
|---|---|
| 10 | surgical stay apparatus |
| 11 | elongated elastic member |
| 12 | first end |
| 13 | second end |
| 14 | hook |
| 15 | handle |
| 16 | hook |
| 17 | handle |
| 18 | patient's tissue |
| 19 | opening |
| 20 | receptacle |
| 21 | user's hand |
| 22 | inclined outer wall |
| 23 | inclined outer wall |
| 24 | rectangular socket |
| 25 | rectangular socket |
| 26 | elastic central section |
| 27 | side wall |
| 28 | side wall |
| 29 | angle |
| 30 | jaw |
| 31 | jaw tip |
| 32 | serrated gripping surface |
| 33 | flange |
| 34 | hinge member |
| 35 | hinge member |
| 36 | convex articulating surface |
| 37 | concave articulating surface |
| 38 | channel |
| 39 | receptacle engaging surface |
| 40 | receptacle engaging surface |
| 41 | receptacle engaging surface |
| 42 | receptacle engaging surface |
| 43 | drape material |

The foregoing embodiments are presented by way of example only; the scope of the present invention is to be limited only by the following claims.

I claim:

1. A surgical retractor comprising:
   a) an elongated elastic member having first and second end portions;
   b) a retractor hook portion connected to the first end portion of the elastic member;
   c) the second end of the elastic member having a receptacle for connecting jaws thereto;
   d) a pair of jaws, each mounted to the elastic member at the receptacle; and
   e) a jaw closing member for urging the jaws to clamp together.

2. The surgical retractor of claim 1 wherein the receptacle includes two sockets at one end of the elastic member and the pair of jaws are attached to the elastic member at the sockets.

3. The surgical retractor of claim 1 wherein the elastic member provides elasticity that urges the jaws to clamp together.

4. The surgical retractor of claim 1 wherein each jaw pivots upon the other.

5. The surgical retractor of claim 4 wherein the jaws pivot, one upon the other at cooperating concave and convex surfaces.

6. The surgical retractor of claim 4 wherein the jaws pivot, one upon the other at cooperating concave and convex articulating surfaces, each jaw having a concave and a convex articulating surface.

7. The surgical retractor of claim 6 wherein the jaws have tip portions that abut when the jaws are closed, and the jaw closing member is positioned in between the jaw tips and the articulating surfaces.

8. The surgical retractor of claim 6 wherein the jaw closure member encircles the jaws.

9. The surgical retractor of claim 1 wherein the jaw closure member is an integral portion of the elongated elastic member.

10. A surgical retractor comprising:
 a) an elongated elastic member having first and second end portions;
 b) a retractor hook portion connected to the first end portion of the elastic member;
 c) the second end of the elastic member having a receptacle for connecting jaws thereto;
 d) a pair of jaws, each mounted to the elastic member at the receptacle at the second end of the elastic member; and
 e) an end portion of the elastic member at the receptacle providing an encircling elastic portion that holds the jaws together.

11. The surgical retractor of claim 10 wherein the encircling portion is an enlarged end portion of the elastic member.

12. The surgical retractor of claim 10 wherein the jaws have tip portions that abut in a closed position and are spaced apart in an open position, and the encircling portion expands when the jaws move to the open position.

13. The surgical retractor of claim 12 wherein each jaw is an integral structure jaw that pivots upon the other jaw.

14. The surgical retractor of claim 10 wherein the jaws pivot, one upon the other at cooperating concave and convex articulating surfaces.

15. The surgical retractor of claim 12 wherein the jaws rotate one with respect to the other at a jaw pivot.

16. The surgical retractor of claim 10 wherein the elastic member has a central axis and an enlarged end portion that includes the receptacle, the receptacle comprising a pair of spaced apart sockets positioned on opposite sides of the central axis of the elastic member.

17. The surgical retractor of claim 16 wherein the jaws are connectable to the sockets by inserting each jaw through the socket from an end of the socket nearest to the second end portion of the elastic member.

18. The surgical retractor of claim 16 wherein the sockets each have a central longitudinal axis and the socket axes define an acute angle.

19. The surgical retractor of claim 16 wherein the sockets are generally rectangular in transverse cross section.

20. A surgical retractor comprising:
 a) an elongated elastic member having first and second end portions;
 b) a retractor hook portion connected to the first end portion of the elastic member;
 c) the second end of the elastic member having a receptacle for connecting jaws thereto;
 d) a pair of jaws, the receptacle including a pair of spaced apart portions for connecting respectively to the jaws; and
 e) a portion of the elastic member next to the spaced apart portions providing elasticity for urging the jaws toward a closed position.

21. The surgical retractor of claim 20 wherein the jaws are freely separable members that are only held together in operating position by the elastic member.

22. The surgical retractor of claim 20 wherein the elastic member has a generally uniform transverse cross sectional configuration along a majority of its length and the receptacle has a larger transverse cross sectional configuration than said generally uniform transverse cross sectional configuration.

23. The surgical retractor of claim 22 wherein the generally uniform transverse cross sectional configuration is generally circular in shape.

24. The surgical retractor of claim 22 wherein the receptacle cross sectional configuration is generally rectangular.

25. A surgical retractor comprising:
 a) an elongated elastic member having first and second end portions;
 b) a retractor hook portion connected to the first end portion of the elastic member;
 c) the second end of the elastic member having a receptacle for connecting jaws thereto;
 d) a pair of jaws that are movable between open and closed position, each jaw attaching to the elastic member at the receptacle, the jaws nesting one against the other at cooperating articulating portions; and
 e) a portion of the receptacle providing elasticity for urging the jaws to the closed position.

26. The surgical retractor of claim 25 wherein the jaws are of the same general size and shape.

27. The surgical retractor of claim 25 wherein the jaws engage at correspondingly shaped concave and convex portions of the jaws that define said articulating portions.

28. The surgical retractor of claim 25 wherein the receptacle and elastic member are of integral construction.

29. The surgical retractor of claim 25 wherein the jaws are each integral members that pivot one upon the other.

30. The surgical retractor of claim 25 wherein the receptacle includes openings that hold the jaws.

\* \* \* \* \*